(12) United States Patent
Guzman

(10) Patent No.: US 8,328,787 B2
(45) Date of Patent: Dec. 11, 2012

(54) PAIN MANAGEMENT METHODS AND APPARATUS

(76) Inventor: Michael F. Guzman, Fortville, IN (US)

( * ) Notice: Subject to any disclaimer, the term of this patent is extended or adjusted under 35 U.S.C. 154(b) by 117 days.

(21) Appl. No.: 12/743,321

(22) PCT Filed: Nov. 24, 2008

(86) PCT No.: PCT/US2008/084501
§ 371 (c)(1),
(2), (4) Date: Jul. 26, 2010

(87) PCT Pub. No.: WO2009/073434
PCT Pub. Date: Jun. 11, 2009

(65) Prior Publication Data
US 2010/0312184 A1    Dec. 9, 2010

Related U.S. Application Data

(63) Continuation-in-part of application No. 11/946,989, filed on Nov. 29, 2007, now Pat. No. 8,211,091.

(60) Provisional application No. 61/057,525, filed on May 30, 2008, provisional application No. 61/107,003, filed on Oct. 21, 2008.

(51) Int. Cl.
*A61M 31/00* (2006.01)
*A61M 5/178* (2006.01)
*A61K 9/22* (2006.01)

(52) U.S. Cl. ............... 604/500; 604/890.1; 604/167.05; 604/506

(58) Field of Classification Search ............... 604/890.1, 604/167.01–167.05
See application file for complete search history.

(56) References Cited

U.S. PATENT DOCUMENTS
5,569,208 A    10/1996   Woelpper et al.
(Continued)

FOREIGN PATENT DOCUMENTS
WO    02-098493 A1    12/2002

OTHER PUBLICATIONS

International preliminary Report on Patentability from PCT/US2008/084501 dated Jun. 10, 2010.
PCT International Search Report for PCT/US2008/084501 completed by the KR Searching Authority on Apr. 17, 2009.
(Continued)

*Primary Examiner* — Nicholas Lucchesi
*Assistant Examiner* — Rebecca E Eisenberg
(74) *Attorney, Agent, or Firm* — Barnes & Thornburg LLP

(57) ABSTRACT

A kit for charging an infusion pump having a reservoir for holding a local anesthetic. The kit includes a first stopcock having an input port, a first input/output port and a second output port and a manual control for selectively coupling either the first input/output port or the second output port to the input port. The kit further includes a second stopcock having an input port, first and second output ports and a manual control for selectively coupling either the first output port or the second output port to the input port. The second output port of the first stopcock is adapted for coupling to the input port of the second stopcock. The kit further includes a syringe adapted to be coupled to the first input/output port of the first stopcock and tubing for coupling the input port of the first stopcock to a source of the liquid and for coupling the output port of the second stopcock to an input port of the pump.

11 Claims, 6 Drawing Sheets

U.S. PATENT DOCUMENTS

| | | |
|---|---|---|
| RE38,074 E | 4/2003 | Recinella et al. |
| 7,232,428 B1 | 6/2007 | Inukai et al. |
| 2002/0019608 A1 | 2/2002 | Mason |
| 2002/0143294 A1 | 10/2002 | Duchon et al. |
| 2003/0004463 A1* | 1/2003 | Reilly et al. .................. 604/124 |
| 2003/0060704 A1 | 3/2003 | Emig et al. |

OTHER PUBLICATIONS http://www.bbraunusa.com/index.cfm?uuid=4E76A7DDD0B759A1E3602055BF3F9F8F.

* cited by examiner

PAIN MANAGEMENT METHODS AND APPARATUS

CROSS-REFERENCE TO RELATED APPLICATIONS

This application is the U. S. national phase of PCT/US2008/084501 filed Nov. 24, 2008, which is a continuation-in-part of, and claims priority to U.S. Ser. No. 11/946,989 filed Nov, 29, 2007. PCT/US2008/084501 also claims priority to U.S. Ser. No. 61/057,525 filed May 30, 2008, and to U.S. Ser. No. 61/107,003 filed Oct. 21, 2008. The disclosures of PCT/US2008/084501, U.S. Ser. No. 11/946,989, U.S. Ser. No. 61/057,525 and U.S. Ser. No. 61/107,003 are incorporated herein by reference.

FIELD OF THE INVENTION

This invention relates to apparatus and methods for the management of pain. It is disclosed in the context of certain self-contained pumps and associated garments for the timed administration of local anesthetics, but it is believed to have other applications as well.

BACKGROUND OF THE INVENTION

Considerable effort has been directed over the past several years at reducing the trauma associated with certain surgical procedures and the recuperation times of patients on whom such surgeries are performed. Among these are, for example, knee replacement, knee reconstruction, shoulder reconstruction, extreme lateral interbody fusion (hereinafter sometimes XLIF), prostate resection, total abdominal hysterectomy, and so on. In some cases, these patients are accident victims. In others, they simply suffer deterioration of the joint being reconstructed or replaced. In any case, more and more of these surgeries are being performed under local, rather than general, anesthetic. The local anesthetic then continues to be administered during the recuperation of the patient for pain management purposes.

There are several benefits associated with such a strategy. For example, the local anesthetics typically used in these cases also have antiseptic attributes owing to their maintenance of pHs in the surgical field that inhibit or retard bacterial growth.

Further, the morbidity/mortality complications associated with administration of general anesthetics are generally avoided by use of local anesthetics in these settings. The locally anesthetized patient typically remains conscious throughout the surgery.

Use of a general anesthetic requires the patient first to regain consciousness. Recovery can be promoted in orthopedic surgical cases, for example, by encouraging the patient to begin exercising the affected joint sooner after completion of the surgery, rather than later. Typically, the locally anesthetized patient can begin exercising the affected joint much sooner after completion of surgery.

BRIEF DESCRIPTION OF THE DRAWINGS

The invention may best be understood by referring to the following detailed description and accompanying drawings which illustrate the invention. In the drawings.

DETAILED DESCRIPTIONS OF ILLUSTRATIVE EMBODIMENTS

Figure 1:
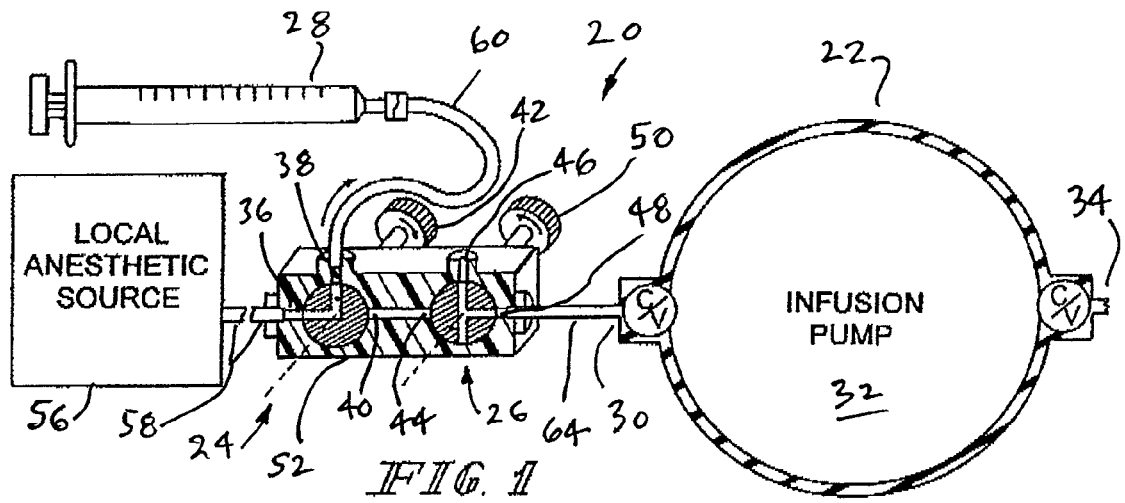
FIG. 1 illustrates a set of components assembled in accordance with the present invention in a first orientation useful in understanding the invention.

Turning now to the drawings, a kit 20 for charging an infusion pump 22 with a local anesthetic to be dispensed includes a first stopcock 24, a second stopcock 26 and a syringe 28. The pump 22 has an input port 30 through which the reservoir 32 of pump 22 is filled and an output port 34 through which local anesthetic in the reservoir 32 is pumped from the pump 22. Typical pumps 22 include the I-Flow Corporation ON-Q PainBuster pump, the Stryker Corporation PainPump®2 pump, and the like. An example of such a syringe 28 is a Beckton, Dickinson 60 ml syringe with luer lock tip.

The first stopcock 24 has an input port 36, a first input/output port 38 and a second output port 40. A manual control 42 is manipulable for selectively coupling either the first input/output port 38 or the second output port 40 to the input port 36. The second stopcock 26 has an input port 44 and first and second output ports 46, 48, respectively. A manual control 50 is manipulable for selectively coupling either the first output port 46 or the second output port 48 to the input port 44. The second output port 40 of the first stopcock 24 is adapted for coupling to the input port 44 of the second stopcock 26. In an illustrative embodiment, the first and second stopcocks 24, 26 are provided in a common body 52. An example of such a dual stopcock arrangement is the Argon Medical Devices, Inc., 041220001A double four way stopcock with male luer lock.

In a typical use, a source 56, such as a 100-200 ml bottle, of local anesthetic, such as ropivicaine, is hung and tapped or spiked with a length of tubing 58, such as a length of vented IV tubing with a drip chamber. An example of a kit for making this connection is the Abbott Laboratories Lifeshield® no. 11961 primary I. V. set with convertible pin, 100 inch (about 2.5 m) with backcheck valve and two CLAVE® ports. The free end of tubing 58 is coupled to port 36 of stopcock 24. A short length of tubing 60 is coupled at one end to port 38 of stopcock 24. Syringe 28 is coupled to the free end of length of tubing 60. Port 40 of stopcock 26 is coupled either through a length of tubing (not shown) or, where stopcocks 24, 26 are provided in a common body 52, through the common body 52, to port 44 of stopcock 26. Port 46 of stopcock 26 is vented to atmosphere. Port 48 of stopcock 26 is coupled through a length of tubing 64 to input port 30 of pump 22. An example of such a length of tubing is the Hospira, Inc., 3229-03, 30 inch (about 76 cm) extension set with Option-Lok®.

Figure 2:
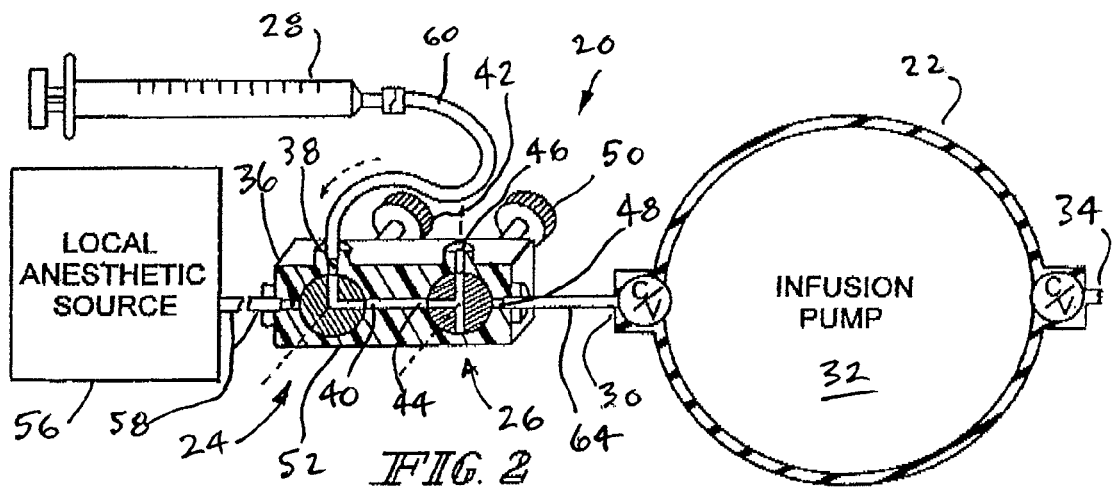
FIG. 2 illustrates a set of components assembled in accordance with the present invention in a second orientation useful in understanding the invention.
Figure 3:
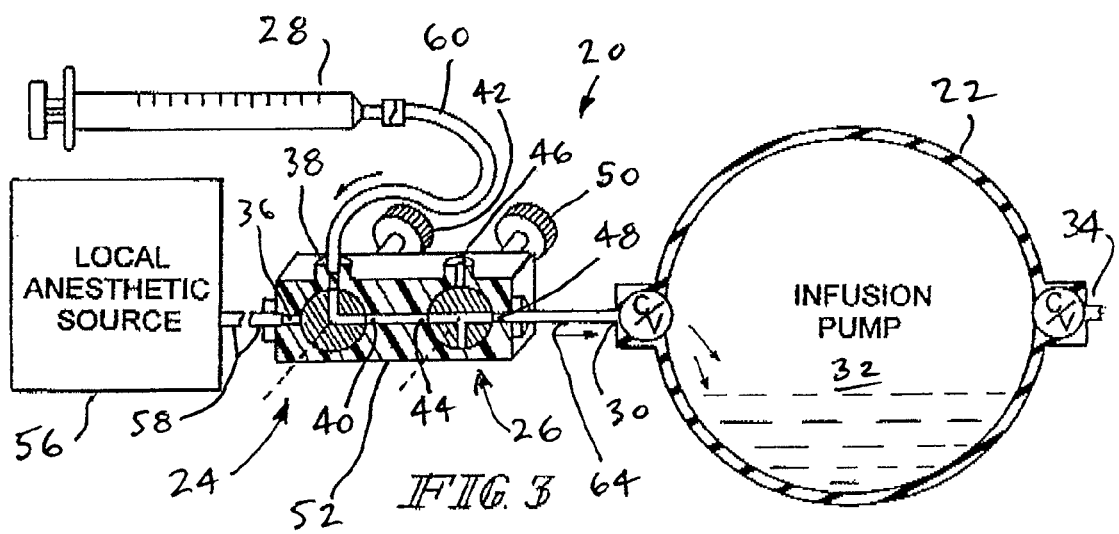
FIG. 3 illustrates a set of components assembled in accordance with the present invention in a third orientation useful in understanding the invention.

Now the user is ready to charge pump 22. The stopcocks 24, 26 are first placed in the orientations illustrated in FIG. 1, coupling the source 56 to syringe 28. The anesthetic is aspirated from source 56 into syringe 28. Any air drawn into syringe 28 is then pumped out by placing stopcocks in the orientations illustrated in FIG. 2, holding the syringe 28 below body 52 with its port up and pushing the plunger of syringe 28 to expel the air through port 46 to atmosphere. When the air has been expelled, the stopcocks 24, 26 are placed in the orientations illustrated in FIG. 3, and the plunger of syringe 28 is pushed, transferring the anesthetic from the body of syringe 28 to the reservoir 32 of pump 22. This process is repeated as often as necessary to transfer the desired amount of anesthetic to reservoir 32. As this is being done, the system remains relatively closed, reducing the likelihood of introduction of bacterial and viral agents and the like into the system. The output port of pump 22 is then coupled to the catheter which is to deliver the anesthetic into the surgical field, and the pump 22 is activated starting the flow of anesthetic to the field.

Figure 4:
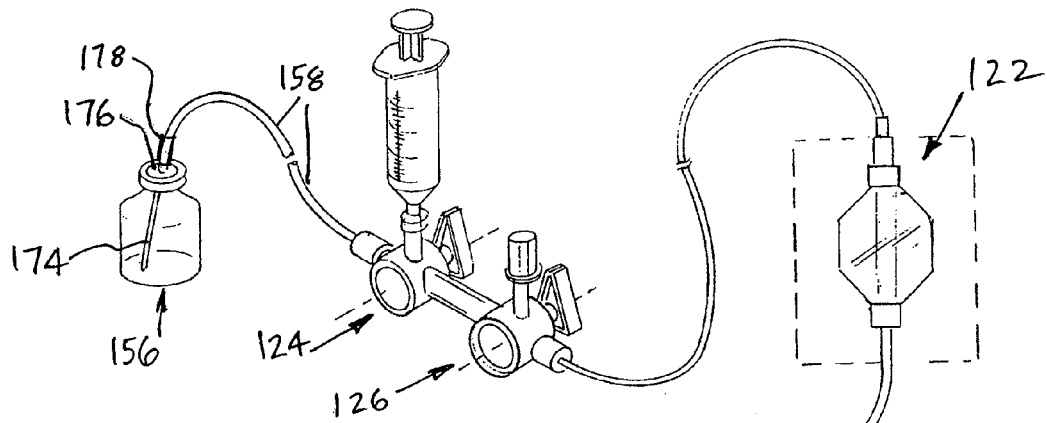
FIG. 4 illustrates a set of components assembled in accordance with the present invention.

In another embodiment illustrated in FIG. 4, the pump 122 is a small, typically 50 ml or 100 ml capacity, pump which is filled from, for example, one or more 30 ml vials 156 of a local anesthetic such as 0.1% ropivicaine or 0.2% ropivicaine. The local anesthetic is then delivered through a flow restrictor 168 which limits the delivery to, for example, 2 ml/hr to a so-called "soaker hose," or side-hole catheter 170, a small gauge catheter having holes provided in its sidewall adjacent the remote end. The catheter 170 is inserted at the surgical site 172 and the local anesthetic is delivered through the catheter 170 continuously at low flow rate to the surgical site 172. In this connection, the vial 156 can be made with a siphon 174 that extends to the bottom of the vial 156 and through the elastomeric cap 176 of the vial 156 and is provided at its outer end with a sterile fitting 178 permitting easy coupling to the inlet end of the conduit 158 to stopcock 124. Operation of the stopcocks 124, 126 then proceeds as described above in connection with stopcocks 24, 26, permitting withdrawal of the local anesthetic from the vial 156 into the syringe 128 and charging of pump 122.

It has been found that, at least with anesthesia associated with certain surgical procedures, such as epidurals for XLIFs, administration of certain local anesthetics such as ropivicaine, hypotension and/or urine retention is a side effect. In many of such cases, it may be desirable to add an effective amount of an antihypertensive, such as, for example, clonidine or any other alpha 2 agonist or compound which works on alpha 2 adrenoceptors in the dorsal horn of the spinal cord with a clinical result which mimics activation of descending inhibitory pathways, thus promoting pain relief, to the local anesthetic being delivered through the pump.

Figure 5:
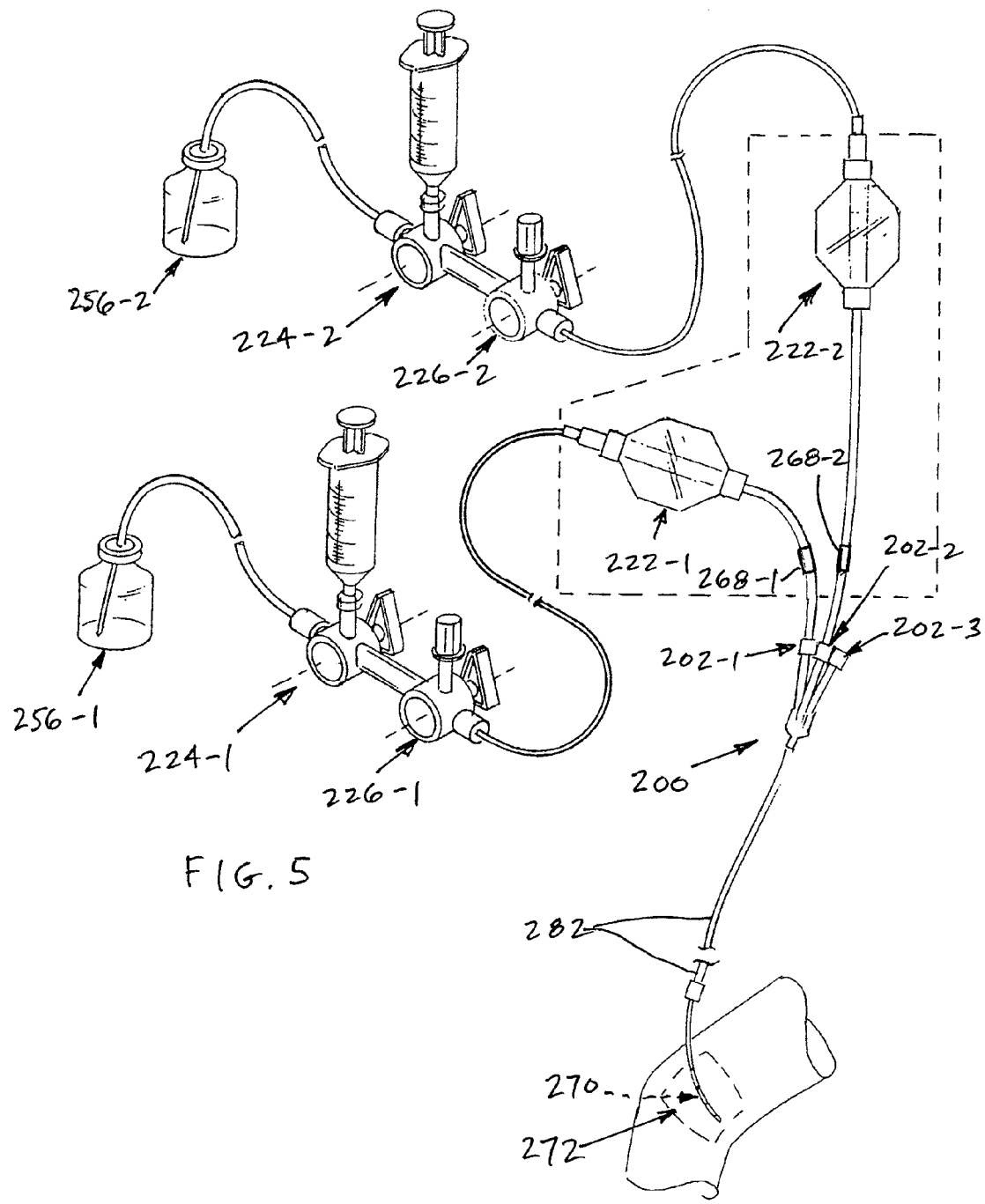
FIG. 5 illustrates a set of components assembled in accordance with the present invention.

In another embodiment illustrated in FIG. 5, a standard central line kit 200 including multiple inlet ports 202-1, 202-2, 202-3 is used to connect a catheter 270 to two pumps 222-1, 222-2 containing two separate concentrations of the local anesthetic. Illustratively, the first pump 222-1 is charged, for example, through a stopcock 224-1, 226-1 assembly from a vial 256-1 containing, for example, 0.1% ropivicaine plus an effective amount of an antihypertensive, again, such as clonidine or any other alpha 2 agonist or compound which works on alpha 2 adrenoceptors in the dorsal horn of the spinal cord with a clinical result which mimics activation of descending inhibitory pathways, thus promoting pain relief. The second pump 222-2 is charged through the same or a separate stopcock 224-2, 226-2 assembly from a vial 256-2 containing, for example, 0.2% ropivicaine. Again, separate flow restrictors 268-1, 268-2 provide flow rates from pumps 222-1, 222-2 when pumps 222-1, 222-2 are activated, that is, when the clamps 280-1, 280-2 blocking flow from pumps 222-1, 222-2, respectively, are released. If the delivery from pump 222-1 through the central line kit 200 and catheter 270 to the surgical site 272 is providing sufficient relief from discomfort to the patient, clamp 280-2 is left on, blocking flow from pump 222-2. If additional pain relief is required, clamp 280-2 is removed, and flow from pump 222-2 combines with flow from pump 222-1 for greater pain relieving capacity at the surgical site 272.

Figure 6:
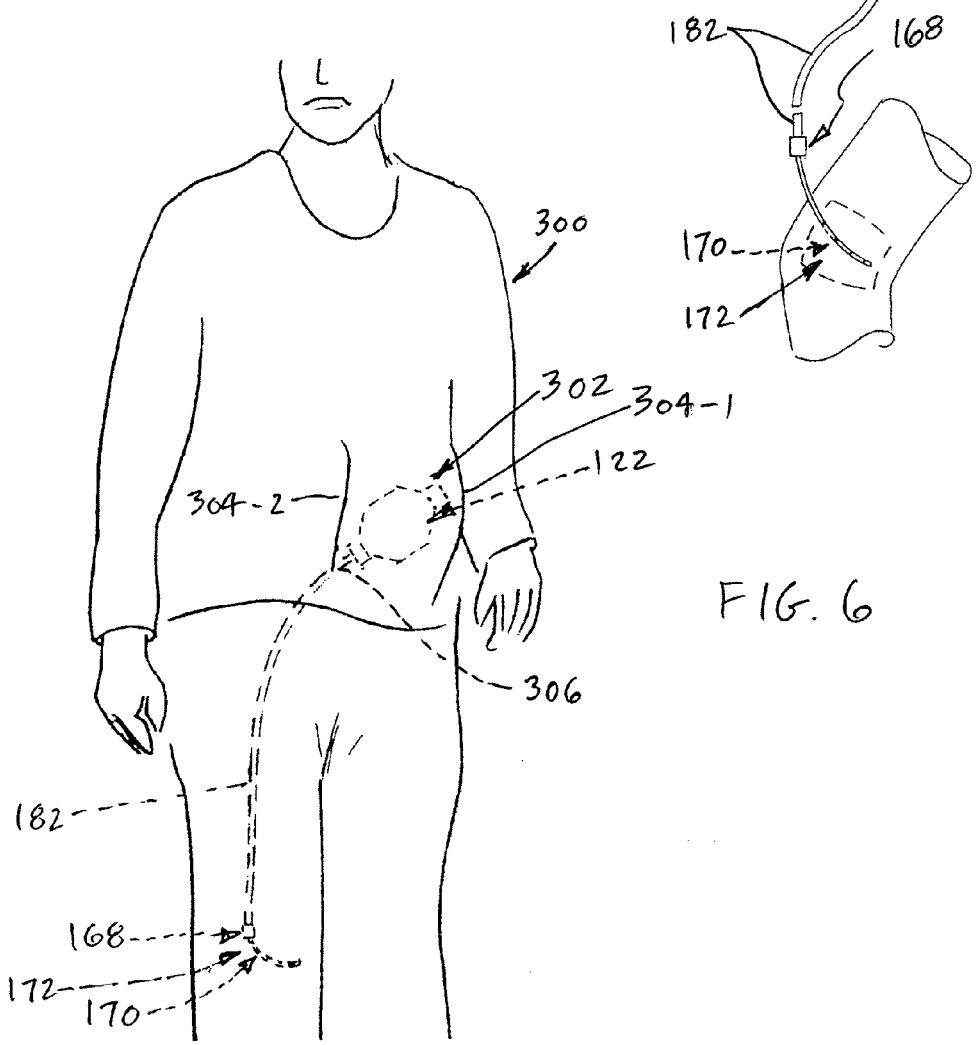
FIG. 6 illustrates apparatus useful in practicing the invention.

Patients who wear pumps 22, 122, 222 during recuperation need suitable means to carry the pumps 22, 122, 222 around. While pumps 122, 222 are smaller, typically 50 ml or 100 ml or so, pumps 22 have capacities of 500 ml. Of course, all of pumps 22, 122, 222 include delivery tubing 182, 282 to conduct the anesthetics being delivered from the pumps 22, 122, 222 to the catheters 70, 170, 270. The pumps 22, 122, 222 and associated tubing 182, 282 must, to the extent possible, be kept from restricting the movement and balance of the patient. It must be remembered that many of the patients who need to wear pumps 22, 122, 222 for pain management are somewhat movement- and coordination-challenged in any event, owing to recent surgery. Additionally, some may be of advanced age. The mass of a pump filled with 500 ml, 100 ml, or even 50 ml of anesthetic, plus the inconvenience of the accompanying delivery tubing 182, 282, may present an impediment to movement, when a recuperating patient may otherwise be encouraged by his or her physician, physical therapist and/or other healthcare provider to move around as an aid to recovery. A garment 300 of the type illustrated in FIG. 6 may aid in overcoming such impediments. The garment 300 is a pullover, sweatshirt or the like, with a central front pocket 302 open at its ends 304-1, 304-2. The pump(s) 22, 122, 222 is (are) placed within the pocket 302. The back side of the pocket, the side adjacent the patient's torso or abdomen, is provided with an opening 306 through which the delivery tubing 182, 282 is threaded. The delivery tubing 182, 282 may then be passed to the surgical site 172, 272, in this case, a knee, by threading the delivery tubing 182, 282 downward past the waistband of the patient's pants to the catheter 170, 270 for delivery of anesthetic to the surgical site 172, 272.

Figure 7:
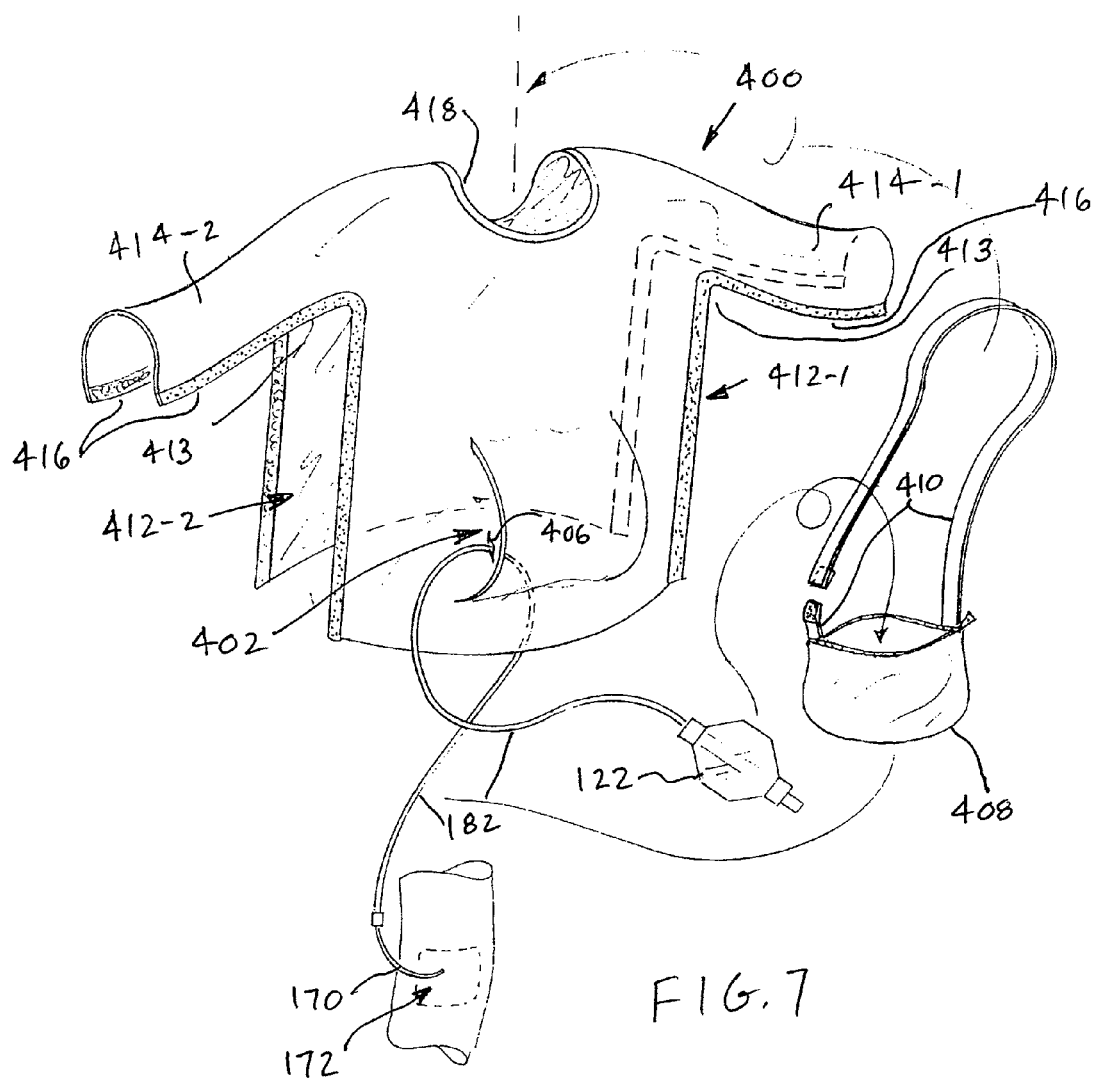
FIG. 7 illustrates apparatus useful in practicing the invention.

In another embodiment illustrated in FIG. 7, a patient may be provided with a pouch 408 provided with a strap 410 for hanging about the patient's neck for carrying a pump 22, 122, 222. Unconstrained, such a pouch may bob back and forth and/or from side to side, compromising the patient's balance. To minimize such motion, the strap 410 may be disconnected, the pouch 408 put in a pocket 402, the strap 410 placed about the patient's neck, and reconnected to the pouch 408. The pump(s) 22, 122, 222 is (are) then placed in the pouch 408, its (their) delivery tubing 182, 282 threaded through an opening 406 for this purpose in the back of the pocket 402, and routed to the catheter 170, 270 at the surgical site 172, 272. Because surgeries of the types discussed herein include, for example, the previously mentioned XLIFs, total abdominal hysterectomies, prostate resections and the like, and orthopedic procedures such as total knee replacements and shoulder surgeries, ease of use of the garment 400 is of some importance. In an effort to make use of the garment 400 easier for the patient, the garment 400 is open up both sides 412-1, 412-2, through the armpits 413 and down the undersides of the arms 414-1, 414-2. The resulting edges 416 are provided with strips of hook-and-loop type fastener material, such as Velcro® brand material. Entry into the garment is thus simplified. The patient slips his or her head through the neck opening 418 and then secures the garment on himself or herself by joining the adjacent edges 416 to the extent desired.

Figure 8:
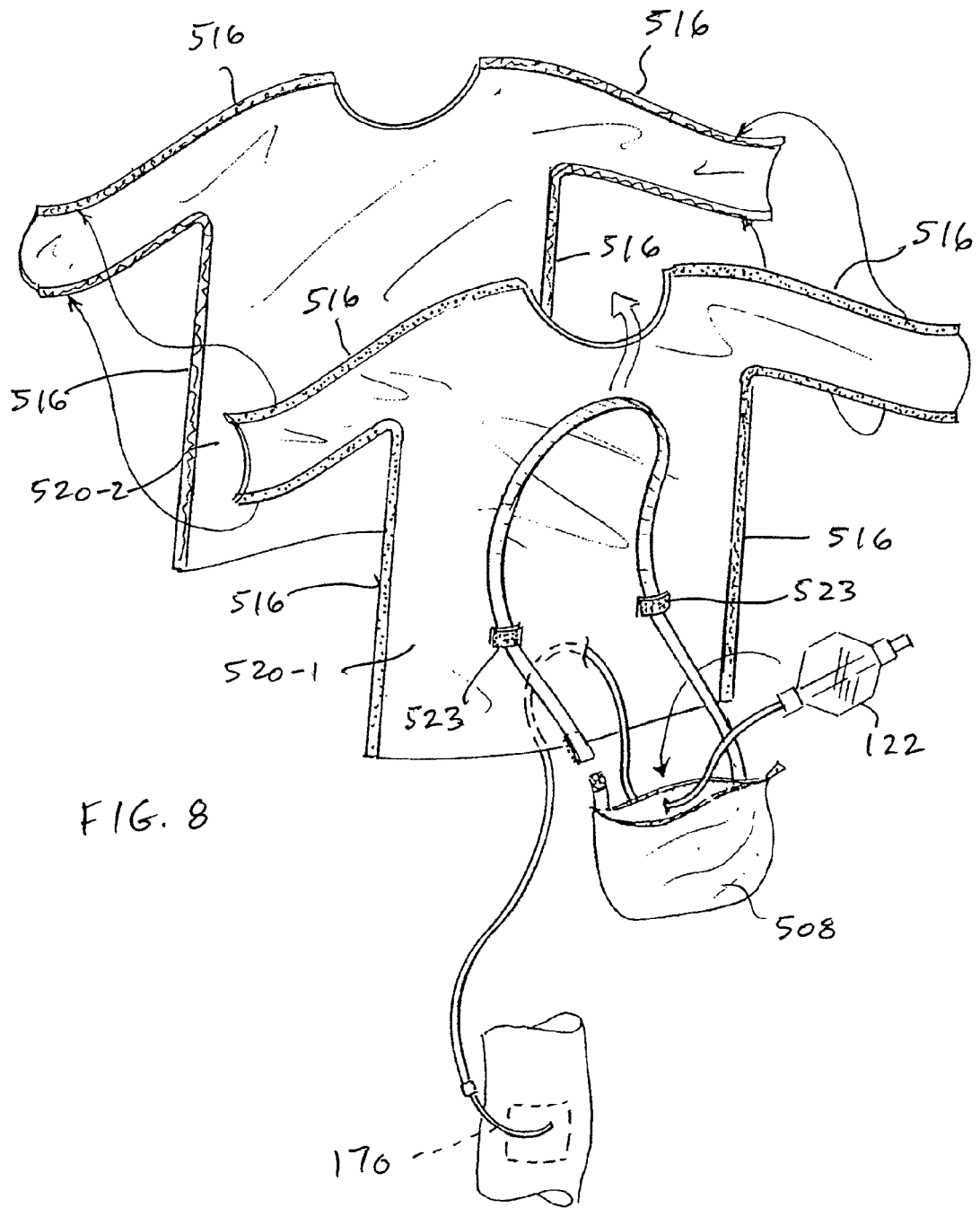
FIG. 8 illustrates apparatus useful in practicing the invention.

In another embodiment of the garment, illustrated in FIG. 8, the garment 500 includes separate front and back panels 520-1, 520-2. Edges 516 of each panel 520-1, 520-2 except for those edges corresponding to the neck hole location, arm hole locations and bottom edge, are provided with strips of hook-and-loop type fastener material permitting as many of such edges 516 of one panel 520-1, 520-2 to be secured together with complementary edges 516 of the opposite panel 520-2, 520-1 to secure the garment 500 on the patient. Additionally, strips of hook-and-loop type fastener material are fashioned into loops 523 on the front panel 520-1, permitting the strap 510 of a pouch 508 to be secured by the loops 523 to restrain the pouch 508 from excessive motion when (a) pump(s) 22, 122, 222 is (are) placed in the pouch 508 and the pouch 508 placed on the patient.

Figure 9:
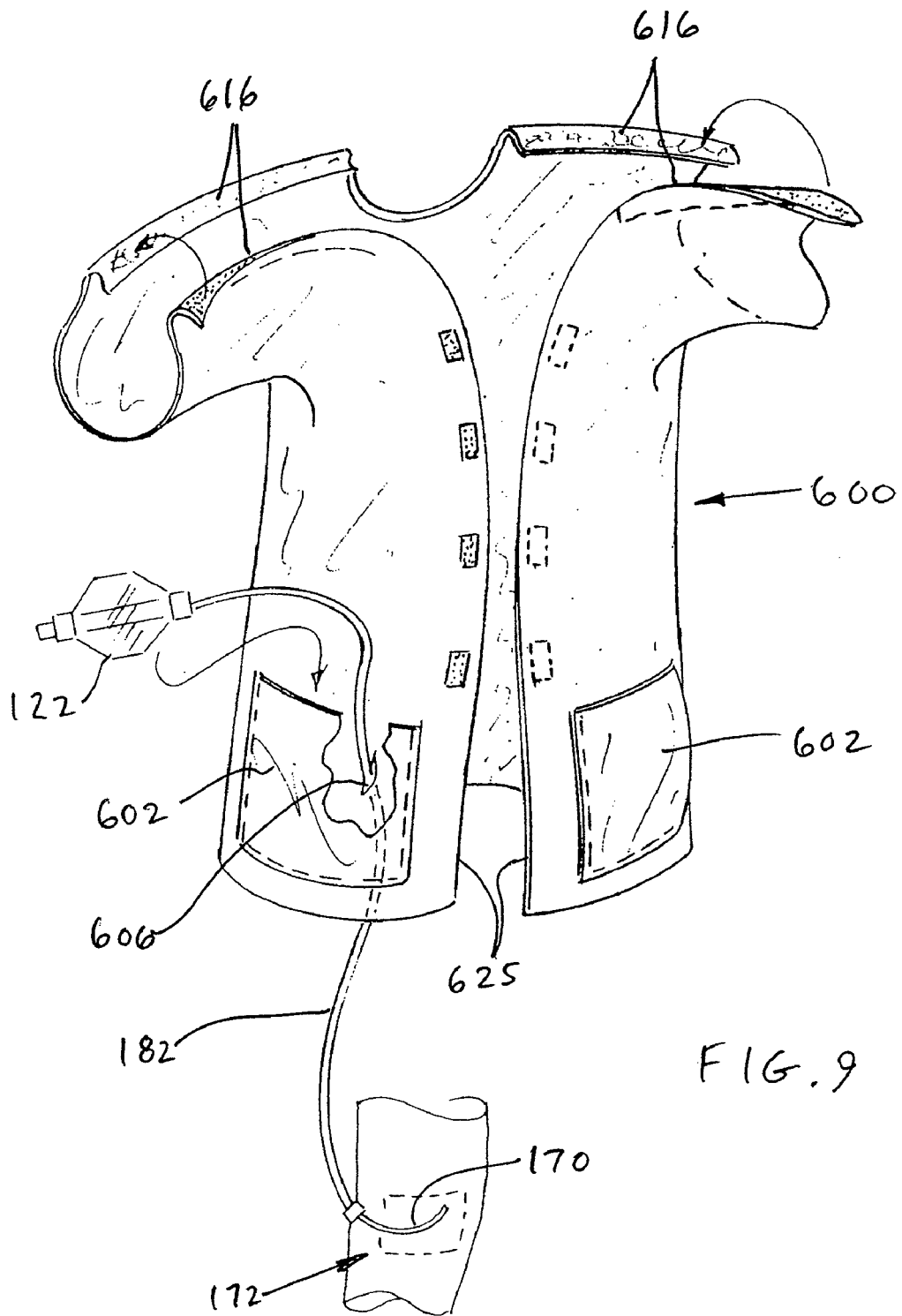
FIG. 9 illustrates apparatus useful in practicing the invention.

In yet another embodiment, illustrated in FIG. 9, a hospital scrub top-like garment 600 is provided with one or more pockets 602. At least one of pockets 602 is provided with an opening 606 for this purpose in the back of the pocket 602. Pocket 602 is of a size to accommodate (a) pump(s) 22, 122, 222. The delivery tubing 182, 282 is threaded through opening 606 and to the surgical site 172, 272 where it is coupled to the delivery catheter 170, 270. In this embodiment, the garment 600 has an open front 625 closable by strips of hook-and-loop type fastener material. Additionally, the shoulders of garment 600 are split from the neck opening to the armholes and the resulting edges 616 are lined with strips of hook-and-loop type fastener material permitting the garment 600 to be secured on the patient.

What is claimed is:

1. A method of filling an infusion pump having a reservoir for holding a liquid which is to be dispensed by the pump, the pump having an input port through which the reservoir is filled and an output port through which liquid in the reservoir is pumped by the pump, the method consisting of coupling a source of the liquid which is to be dispensed by the pump to an input port of a dual stopcock also having an input/output port, a first output port and a second output port, coupling the first output port of the dual stopcock to the input port of the pump, coupling a syringe to the input/output port of the dual stopcock, drawing from the source into the syringe an amount of liquid to be transferred to the pump, operating the stopcock to couple the syringe to the input port of the pump, and operating the syringe to transfer liquid from the syringe to the pump.

2. A method of filling an infusion pump having a reservoir for holding a liquid which is to be dispensed by the pump, the pump having an input port through which the reservoir is filled and an output port through which liquid in the reservoir is pumped by the pump, the method consisting of coupling a source of the liquid which is to be dispensed by the pump to an input port of a dual stopcock also having an input/output port, a first output port and a second output port, coupling the first output port of the dual stopcock to the input port of the pump, coupling a syringe to the input/output port of the dual stopcock, repeatedly drawing from the source into the syringe an amount of liquid to be transferred to the pump, operating the stopcock to couple the syringe to the input port of the pump, and operating the syringe to transfer liquid from the syringe to the pump until a desired amount of the liquid has been transferred to the pump.

3. A method of filling an infusion pump having a reservoir for holding a liquid which is to be dispensed by the pump, the pump having an input port through which the reservoir is filled and an output port through which liquid in the reservoir is pumped by the pump, the method consisting of coupling a source of the liquid which is to be dispensed by the pump to an input port of a dual stopcock also having an input/output port, a first output port and a second output port, coupling the first output port of the dual stopcock to the input port of the pump, coupling a syringe to the input/output port of the dual stopcock, repeatedly drawing from the source into the syringe an amount of liquid to be transferred to the pump, drawing air into the syringe as the liquid is drawn into the syringe, operating the dual stopcock to couple the syringe to the second output port of the dual stopcock, orienting the syringe so that the air captured in the syringe can be expelled from the syringe substantially without expelling any of the liquid, operating the syringe and the dual stopcock to expel air from the syringe through the second output port of the stopcock, repeatedly operating the stopcock to couple the syringe to the input port of the pump, and repeatedly operating the syringe to transfer liquid from the syringe to the pump until a desired amount of the liquid has been transferred to the pump.

4. A method of filling an infusion pump having a reservoir for holding a liquid which is to be dispensed by the pump, the pump having an input port through which the reservoir is filled and an output port through which liquid in the reservoir is pumped by the pump, the method consisting of coupling a source of the liquid which is to be dispensed by the pump to an input port of a dual stopcock also having an input/output port, a first output port and a second output port, coupling the first output port of the dual stopcock to the input port of the pump, coupling a syringe to the input/output port of the dual stopcock, repeatedly drawing from the source into the syringe an amount of liquid to be transferred to the pump, repeatedly drawing air into the syringe as the liquid is drawn into the syringe, repeatedly operating the dual stopcock to couple the syringe to the second output port of the dual stopcock, repeatedly orienting the syringe so that the air captured in the syringe can be expelled from the syringe substantially without expelling any of the liquid, repeatedly operating the syringe and the dual stopcock to expel air from the syringe through the second output port of the stopcock, repeatedly operating the stopcock to couple the syringe to the input port of the pump, and repeatedly operating the syringe to transfer liquid from the syringe to the pump until a desired amount of the liquid has been transferred to the pump.

5. A method of filling an infusion pump having a reservoir for holding a liquid which is to be dispensed by the pump, the pump having an input port through which the reservoir is filled and an output port through which liquid in the reservoir is pumped by the pump, the method consisting of coupling a source of the liquid which is to be dispensed by the pump to an input port of a dual stopcock also having an input/output port, a first output port and a second output port, coupling the first output port of the dual stopcock to the input port of the pump, coupling a syringe to the input/output port of the dual stopcock, drawing air into the syringe as the liquid is drawn into the syringe, operating the dual stopcock to couple the syringe to the second output port of the dual stopcock, orienting the syringe so that the air captured in the syringe can be expelled from the syringe substantially without expelling any of the liquid, and operating the syringe and the dual stopcock to expel air from the syringe through the second output port of the stopcock.

6. A method of filling an infusion pump having a reservoir for holding a liquid which is to be dispensed by the pump, the pump having an input port through which the reservoir is filled and an output port through which liquid in the reservoir is pumped by the pump, the method consisting of coupling a source of the liquid which is to be dispensed by the pump to an input port of a first stopcock also having a first input/output port and a second output port, coupling the second output port of the first stopcock to an input port of a second stopcock having first and second output ports, coupling the first output port of the second stopcock to the input port of the pump, coupling a syringe to the first input/output port of the first stopcock, operating the first stopcock to couple the input port of the first stopcock to the first input/output port of the first stopcock, drawing from the source into the syringe an amount of liquid to be transferred to the pump, operating the first and second stopcocks to couple the syringe to the input port of the pump, and operating the syringe to transfer liquid from the syringe to the pump.

7. A method of filling an infusion pump having a reservoir for holding a liquid which is to be dispensed by the pump, the pump having an input port through which the reservoir is filled and an output port through which liquid in the reservoir is pumped by the pump, the method consisting of coupling a source of the liquid which is to be dispensed by the pump to an input port of a first stopcock also having a first input/output port and a second output port, coupling the second output port of the first stopcock to an input port of a second stopcock having first and second output ports, coupling the first output port of the second stopcock to the input port of the pump, coupling a syringe to the first input/output port of the first stopcock, operating the first stopcock to couple the input port of the first stopcock to the first input/output port of the first stopcock, operating the syringe to transfer liquid from the syringe to the pump, repeatedly drawing from the source into the syringe an amount of liquid to be transferred to the pump, repeatedly operating the first and second stopcocks to couple the syringe to the input port of the pump, and repeatedly operating the syringe to transfer liquid from the syringe to the pump until a desired amount of the liquid has been transferred to the pump.

8. A method of filling an infusion pump having a reservoir for holding a liquid which is to be dispensed by the pump, the pump having an input port through which the reservoir is filled and an output port through which liquid in the reservoir is pumped by the pump, the method consisting of coupling a source of the liquid which is to be dispensed by the pump to an input port of a first stopcock also having a first input/output port and a second output port, coupling the second output port of the first stopcock to an input port of a second stopcock having first and second output ports, coupling the first output port of the second stopcock to the input port of the pump, coupling a syringe to the first input/output port of the first stopcock, operating the first stopcock to couple the input port of the first stopcock to the first input/output port of the first stopcock, operating the syringe to transfer liquid from the syringe to the pump, drawing air into the syringe as the liquid is drawn into the syringe, operating the second stopcock to couple the syringe to the second output port of the second stopcock, orienting the syringe so that the air captured in the syringe can be expelled from the syringe substantially without expelling any of the liquid, operating the syringe and the first and second stopcocks to expel air from the syringe through the second output port of the second stopcock, repeatedly operating the first and second stopcocks to couple the syringe to the input port of the pump, and repeatedly operating the syringe to transfer liquid from the syringe to the pump until a desired amount of the liquid has been transferred to the pump.

9. A method of filling an infusion pump having a reservoir for holding a liquid which is to be dispensed by the pump, the pump having an input port through which the reservoir is filled and an output port through which liquid in the reservoir is pumped by the pump, the method consisting of coupling a source of the liquid which is to be dispensed by the pump to an input port of a first stopcock also having a first input/output port and a second output port, coupling the second output port of the first stopcock to an input port of a second stopcock having first and second output ports, coupling the first output port of the second stopcock to the input port of the pump, coupling a syringe to the first input/output port of the first stopcock, operating the first stopcock to couple the input port of the first stopcock to the first input/output port of the first stopcock, operating the syringe to transfer liquid from the syringe to the pump, repeatedly drawing from the source into the syringe an amount of liquid to be transferred to the pump, repeatedly drawing air into the syringe as the liquid is drawn into the syringe, operating the first and second stopcocks to couple the syringe to the second output port of the second stopcock, orienting the syringe so that the air captured in the syringe can be expelled from the syringe substantially without expelling any of the liquid, repeatedly operating the syringe to expel air from the syringe through the second output port of the second stopcock, repeatedly operating the first and second stopcocks to couple the syringe to the input port of the pump, and repeatedly operating the syringe to transfer liquid from the syringe to the pump until a desired amount of the liquid has been transferred to the pump.

10. A method of filling an infusion pump having a reservoir for holding a liquid which is to be dispensed by the pump, the pump having an input port through which the reservoir is filled and an output port through which liquid in the reservoir is pumped by the pump, the method consisting of coupling a source of the liquid which is to be dispensed by the pump to an input port of a first stopcock also having a first input/output port and a second output port, coupling the second output port of the first stopcock to an input port of a second stopcock having first and second output ports, coupling the first output port of the second stopcock to the input port of the pump, coupling a syringe to the first input/output port of the first stopcock, operating the first stopcock to couple the input port of the first stopcock to the first input/output port of the first stopcock, drawing from the source into the syringe an amount of liquid to be transferred to the pump, drawing air into the syringe as the liquid is drawn into the syringe, operating the first and second stopcocks to couple the syringe to the second output port of the second stopcock, orienting the syringe so that the air captured in the syringe can be expelled from the syringe substantially without expelling any of the liquid, operating the syringe to expel air from the syringe through the second output port of the second stopcock, operating the first and second stopcocks to couple the syringe to the input port of the pump, and operating the syringe to transfer liquid from the syringe to the pump.

11. A method of filling an infusion pump having a reservoir for holding a liquid which is to be dispensed by the pump, the pump having an input port through which the reservoir is filled and an output port through which liquid in the reservoir is pumped by the pump, the method consisting of coupling a source of the liquid which is to be dispensed by the pump to an input port of a dual stopcock also having an input/output port, a first output port and a second output port, the first and second stopcocks of the dual stopcock provided in a common body, coupling the first output port of the dual stopcock to the input port of the pump, coupling a syringe to the input/output port of the dual stopcock, drawing air into the syringe as the liquid is drawn into the syringe, operating the dual stopcock to couple the syringe to the second output port of the dual stopcock, orienting the syringe so that the air captured in the syringe can be expelled from the syringe substantially without expelling any of the liquid, and operating the syringe and the dual stopcock to expel air from the syringe through the second output port of the stopcock, operating the first and second stopcocks to couple the syringe to the input port of the pump, and operating the syringe to transfer liquid from the syringe to the pump.

* * * * *